(12) United States Patent
Chevalier et al.

(10) Patent No.: US 6,630,131 B2
(45) Date of Patent: Oct. 7, 2003

(54) COMPOSITION CONTAINING A MIXED SILICATE, A POLYSACCHARIDE AND CROSSLINKED POLY(2-ACRYLAMIDO-2-METHYL-PROPANE-SULPHONIC ACID) POLYMER

(75) Inventors: Veronique Chevalier, Villecresnes (FR); Valerie Hurel, Gif/S/Yvette (FR)

(73) Assignee: L'Oreal, Paris (FR)

( * ) Notice: Subject to any disclaimer, the term of this patent is extended or adjusted under 35 U.S.C. 154(b) by 66 days.

(21) Appl. No.: 09/985,758

(22) Filed: Nov. 6, 2001

(65) Prior Publication Data
US 2003/0108497 A1 Jun. 12, 2003

(30) Foreign Application Priority Data
Nov. 6, 2001 (FR) ............................................. 00 14175

(51) Int. Cl.[7] ............................. A61K 7/42; A61K 7/44; A61K 7/00

(52) U.S. Cl. ............................. 424/59; 424/60; 424/400; 424/401

(58) Field of Search ............................. 424/59, 60, 400, 424/401

(56) References Cited

U.S. PATENT DOCUMENTS 5,112,391 A    5/1992   Owen et al. .................. 75/772

Primary Examiner—Shelley A. Dodson
(74) Attorney, Agent, or Firm—Oblon, Spivak, McClelland, Maier & Neustadt, P.C.

(57) ABSTRACT

The invention relates to a composition containing at least one mixed silicate, at least one polysaccharide and at least one crosslinked poly(2-acrylamido-2-methylpropanesulphonic acid) polymer which is at least 90% neutralized, having use in the cosmetic field as a tightening agent, in particular for tightening the skin and smoothing it so as to immediately attenuate the wrinkles and/or fine lines on the skin.

28 Claims, No Drawings

COMPOSITION CONTAINING A MIXED SILICATE, A POLYSACCHARIDE AND CROSSLINKED POLY(2-ACRYLAMIDO-2-METHYL-PROPANE-SULPHONIC ACID) POLYMER

BACKGROUND OF THE INVENTION

FIELD OF THE INVENTION

The present invention relates to a composition containing a mixed silicate, a polysaccharide, and a crosslinked poly(2-acrylamido-2-methylpropanesulphonic acid) polymer, and the preparation and uses of the composition, in particular in the cosmetic field as a tightening agent, and for reducing and/or removing, and reducing and/or removing the appearance of, wrinkles and/or fine lines from the skin.

DISCUSSION OF THE BACKGROUND

It is known to use clays and in particular mixed silicates, in cosmetic compositions. These silicates are known for their thixotropic properties and may be used as thickening, film-forming, emulsifying, adsorbent and/or absorbent agents. They are excellent gelling agents which are resistant to extreme pH and temperature conditions, and their fields of application, outside the cosmetic field, are vast (for example paints, agriculture, building products).

Patent WO-A-97/3 1619 describes cleansing and astringent cosmetic compositions containing, inter alia, laponite which belongs to the mixed silicate family and more particularly to the class of sodium and magnesium silicates. Laponites are synthetic stratified colloidal silicate used for their oil-absorbing properties. Such a laponite may be used as thickening and/or gelling agent in cosmetic compositions as described in Patent Application EP-A-412 449.

In addition, mixed silicates such as laponite are described as tightening agents in the document EP-A-1 008 340.

Unfortunately, compositions containing mixed silicates, most particularly when they are in the form of an emulsion (composition comprising at least one aqueous phase and t least one oily phase dispersed in one another) and when they contain more than 3% of mixed silicates, exhibit insufficient stability, which makes the incorporation of such a quantity of these silicates into cosmetic compositions difficult because the latter must have excellent stability during their entire commercial shelf life. The instability of emulsions containing more than 3% by weight of mixed silicates such as laponite occurs after a few days or even one to two weeks, and it manifests itself, inter alia, by a separation of the oily and aqueous phases, by a variation in color and/or in odor, and by a change in viscosity during the period of storage.

The document EP-A-1 008 340 describes the combination of laponite and xanthan gum. However, above 3% laponite, the composition containing this combination no longer has sufficient stability to constitute a commercially viable product.

SUMMARY OF THE INVENTION

The Inventors have discovered, surprisingly, that the combining of a polysaccharide and a polymer derived from 2-acrylamido-2-methylpropanesulphonic acid with one or more mixed silicates makes it possible to obtain compositions, including emulsions, having very good stability over time.

DETAILED DESCRIPTION OF THE INVENTION

One subject of the present invention is therefore a composition containing at least one mixed silicate, at least one polysaccharide, and at least one crosslinked poly(2-acrylamido-2-methylpropanesulphonic acid) polymer, which polymer is at least 90% neutralized. Methods of preparation and use of the invention compositions also make up part of the invention.

The composition according to the invention has the advantage of being particularly stable even when the quantity of mixed silicate exceeds 3% by weight, and even when it exists in the form of an emulsion, in particular in the form of an oil-in-water emulsion. It remains completely stable at any temperature after two months of storage or more, that is to say that macroscopically, no change in color, odor, or rising of oil (phase separation), or change in viscosity, or variation in pH, is observed, and that, microscopically, no change in appearance is observed.

According to a preferred embodiment of the invention, the composition of the invention constitutes a cosmetic and/or dermatological composition and comprises a physiologically acceptable medium. The expression "physiologically acceptable medium" is understood here to mean a medium compatible with the skin, including the scalp, the lips and the hair.

The expression mixed silicate is understood to mean, in the present invention, any silicates of natural or synthetic origin containing several (two or more) types of cation chosen from alkali metals (for example Na, Li, K) or alkaline-earth metals (for example Be, Mg, Ca), transition metals and aluminum.

These mixed silicates may be of natural or synthetic origin, and may be chosen from montmorillonites, hectorites, bentonites, beidellite, saponites. According to a preferred embodiment of the invention, the mixed silicates used are more particularly chosen from hectorites and bentonites, and better still from laponites.

To ensure good cosmetic properties, these silicates should be preferably provided in a finely divided form, and in particular in the form of particles having a mean size ranging from 5 nm to 1 $\mu$m (from 5 to 1,000 nm), and preferably from 20 nm to 600 nm. The particles of mixed silicates may have the shape of discs or sheets. Accordingly, the expression mean particle size is understood here to mean the mean size, in numerical terms, of the longest dimension (length) of these discs or sheets. Particles in the form of discs or sheets preferably have a thickness ranging from about 0.5 to 5 nm.

Phyllosilicates, namely silicates having a structure in which the tetrahedra $SiO_4$ are organized into sheets between which the metal cations become enclosed, are preferably used in the present invention.

A silicate family which is particularly preferred in the compositions of the present invention is that of the laponites. Laponites are silicates of magnesium, sodium and optionally lithium, having a structure in layers which is similar to that of montmorillonites. Laponite is the synthetic form of the natural mineral called "hectorite". The synthetic origin of this silicate family has a considerable advantage compared with the natural form because it allows good control of the composition of the product. In addition, laponites have the advantage of having a particle size which is much less than those of natural hectorite and bentonite.

As laponites, there may be mentioned in particular the products sold by the company Laporte under the name Laponite XLS, Laponite XLG, Laponite RD, Laponite RDS (these products are silicates of sodium and magnesium and silicates of sodium, lithium and magnesium).

As mixed silicates, there may also be mentioned bentonites such as the product sold under the name Bentone HC by the company RHEOX; the silicates of magnesium and aluminum, in particular hydrated, such as the product sold by the company Vanderbilt Company under the name Veegum ultra, or calcium silicates and in particular that in synthetic form sold by the company Celite under the name Micro-cel C.

The quantity of mixed silicate(s) in the composition of the invention may range, for example, from 0.01 to 10% by weight and greater, preferably from 0.05 to 5% by weight and better still from 1 to 5% by weight relative to the total weight of the composition. In addition, amounts greater than 3% by weight are preferred including 3.5, 4, 4.5 and 5% by weight.

Polysaccharides which can be used in the composition of the invention include cellulose derivatives; galactomannans (polysaccharides mainly composed of galactose and mannose units) and their derivatives, such as guar gum, carob gum, and guar gums modified in particular by grafting an alkyl group; algal extracts such as agar, carrageenans, alginates; plant exudates such as gum arabic, karaya gum, gum tragacanth and ghatti gum; microbial exudates such as xanthan gum, gellan gum, rhamsan gum; and mixtures thereof. According to a preferred embodiment of the invention, the polysaccharide used is a gum and in particular xanthan gum.

The quantity of polysaccharide(s) in the composition of the invention preferably ranges from 0.01 to 8% by weight, preferably from 0.5 to 5% by weight and better still from 0.1 to 3% including 0.5, 1, 1.5, 2 and 2.5% by weight relative to the total weight of the composition.

In the present application, the expression "crosslinked poly(2-acrylamido-2-methylpropanesulphonic acid) polymer which is at least 90% neutralized" is understood to mean a homopolymer derived from 2-acrylamido-2-methylpropanesulphonic acid, which is crosslinked and which is practically fully neutralized or which is fully neutralized. This definition is understood by those of ordinary skill in the art. These polymers are water-soluble or are swellable in water.

The polymers used in the composition of the invention are generally characterized in that they comprise, randomly distributed:

a) from 90 to 99.9 by weight of units having the following general formula (I):

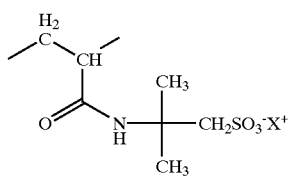

(I)

in which $X^+$ denotes a cation or a mixture of cations, it being possible for at most 10 mol % of the cations $X^+$ to be protons $H^+$;

b) from 0.01 to 10% by weight of crosslinking units obtained from at least one monomer having at least two olefin double bonds, the proportions by weight being defined relative to the total weight of the polymer.

Preferably, the polymers of the invention comprise a number of units of formula (I) in a sufficiently high quantity to obtain particles of polymer whose hydrodynamic volume in solution in water has a radius ranging from 10 to 500 nm and whose distribution is homogeneous and unimodal.

The polymers used in the composition according to the invention which are particularly preferred comprise from 98 to 99.5% by weight of units of formula (I) and from 0.5 to 2% by weight of crosslinking units.

In formula (I) $X^+$ represents a cation or a mixture of cations, including those chosen in particular from a proton, an alkali metal cation, a cation which is the equivalent of that of an alkaline-earth metal or the ammonium ion.

In a preferred embodiment, 90 to 100 mol% of the cations are $NH_4^+$ cations and 0 to 10 mol % are protons $(H)^+$.

The crosslinking monomers having at least two olefin double bonds include, for example, propylene glycol diallyl ether, polyglycol diallyl ether, triethylene glycol divinyl ether, hydroquinone diallyl ether, tetraallyl oxethanoyl or other polyfunctional allyl or vinyl ether alcohols, tetraethylene glycol diacrylate, triallylamine, trimethylolpropane diallyl ether, methylene-bisacrylamide or divinylbenzene.

The crosslinking monomers having at least two olefin double bonds are preferably chosen from those corresponding to the general formula (II):

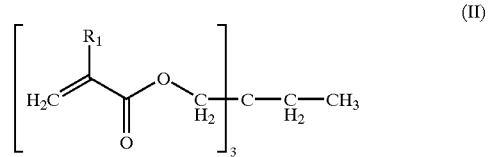

(II)

in which $R_1$, denotes a hydrogen atom or a $C_1$–$C_4$ alkyl, and more particularly methyl. The crosslinking monomer is preferably trimethylolpropane triacrylate (compound of formula II where $R_1$ is hydrogen).

The invention polymers that are particularly preferred are those having a viscosity measured with a BROOKFIELD viscometer, No. 4 rotor, at a rotating speed of 100 revolutions/minute in a solution in water at 2% and at a temperature of about 25° C., greater than or equal 10 to 1000 cps (or 1000 mPa·s) and more preferably ranging from 5000 to 40000 cps (5000 to 40000 mPa·s) and more particularly from 6500 to 35000 cps (6500 to 35000 mPa·s).

The crosslinked poly(2-acrylamido-2-methylpropanesulphonic acid) used in the composition of the invention may be obtained according to a method comprising the following steps:

(a) the 2-acrylamido-2-methylpropanesulphonic acid monomer is dispersed or dissolved in free form in a solution of tert-butanol or of water and tert-butanol;

(b) the monomer solution or dispersion obtained in (a) is neutralized with one or more inorganic or organic bases, preferably aqueous ammonia $NH_3$, in a quantity which makes it possible to obtain a level of neutralization of the sulphonic acid functional groups of the polymer ranging from 90 to 100;

(c) the crosslinking monomer(s) is (are) added to the solution or dispersion obtained in (b);

(d) a conventional free-radical polymerization is carried out in the presence of free radical initiators at a temperature ranging from 10 to 150° C.; the polymer precipitating in the tert-butanol-based solution or dispersion.

The crosslinked poly(2-acrylamido-2-methylpropanesulphonic acid) used in the composition of the invention may be in particular the product marketed by the company Hoechst under the trade name "Hostacerin AMPS" (CTFA name: ammonium polyacryldimethyltauramide).

The crosslinked poly(2-acrylamido-2-methylpropanesulphonic acid) used in the composition of the invention is preferably present in a quantity ranging from 0.1 to 10% by weight, better still from 0.2 to 5% by weight and more preferably from 0.2 to 2% by weight including 0.5, 1, 1.5 and 1.7% by weight relative to the total weight of the composition.

The composition of the invention contains at least one aqueous medium which may constitute the physiologically acceptable medium for a topical composition. This aqueous medium may comprise, in addition to water, optionally additives such as polyols such as glycerin, glycols (butylene glycol, propylene glycol, polyethylene glycols), sugars and lower alcohols comprising from 1 to 6 and preferably from 1 to 4 carbon atoms such as ethanol or isopropanol. When the composition is in the form of an emulsion, this aqueous medium constitutes the aqueous phase of the emulsion.

The compositions according to the invention may constitute in particular a composition for topical application such as a cosmetic or dermatological composition, and they may be provided in any galenic forms normally used for a topical application, in particular in the form of an optionally gelled aqueous solution, in the form of optionally two-phase lotions, in the form of oil-in-water (O/W) or water-in-oil (W/O) or multiple emulsions, or in the form of a dispersion of oil in an aqueous phase with the aid of spherules, it being possible for these spherules to be polymeric nanoparticles such as nanospheres and nanocapsules, or better still lipid vesicles of the ionic and/or nonionic type. These compositions may be prepared according to customary methods known to those skilled in the art. They may be fluid to a greater or lesser degree and look like, e.g., a cream, an ointment, a milk, a lotion, a serum or a mousse. They may be optionally applied to the skin in the form of an aerosol. They may also be provided in the form of a paste which is hard to a greater or lesser degree, for example in the form of a stick. They may be used, for example, as care products and/or as make-up products for the skin.

The composition of the invention may also contain adjuvants useful in the cosmetic, pharmaceutical or dermatological fields, such as hydrophilic or lipophilic gelling agents, hydrophilic or lipophilic active agents, preservatives, antioxidants, solvents, perfumes, fillers, sequestrants (EDTA), pH-regulating agents (acid or base), bactericides, odor absorbers, coloring matter (pigments, colorants), salts. The quantities of these various adjuvants are those conventionally used in the field considered, and are, for example, from 0.01 to 10% of the total weight of the composition. These adjuvants, depending on their nature, may be introduced into the fatty phase or into the aqueous phase of the composition. These adjuvants as well as their concentrations should be such that they do not modify the property sought out for the composition of the invention.

As active agents, there may be mentioned vitamins such as, for example, vitamins A (retinol), C (ascorbic acid), B3 or PP (niacinamide), B5 (panthenol), E (tocopherol), K1, and the derivatives of these vitamins and in particular their esters; keratolytic or prodesquamatory agents such as hydroxy acids (α-hydroxy acids and β-hydroxy acids) such as glycolic acid, citric acid, lactic acid, salicylic acid and derivatives thereof; anti-free radical agents; sunscreens; moisturizing agents such as polyols; ceramides; retinoids; and tightening polymers, in particular organic polymers, such as latexes, protein hydrolysates and chitine derivatives; RHEA and its derivatives such as alpha-hydroxy-DHEA; coenzyme Q10, and mixtures thereof.

As sunscreens, the composition of the invention may comprise the chemical UVA-and UVB-screening agents which can be normally used in the cosmetic field, including insoluble organic UV-screening agents, that is to say organic UV-screening agents whose solubility in water is less than 0.1% by weight and whose solubility in liquid paraffin is less than 0.1% by weight.

As sunscreens, there may also be used inorganic screening agents such as titanium dioxide and zinc oxide, coated or otherwise.

It is also possible to use a mixture of these various sorts of screening agents.

As UVB-screening agents, included are for example:
(1) derivatives of salicylic acid, in particular homomenthyl salicylate and octyl salicylate;
(2) derivatives of cinnamic acid, in particular 2-ethylhexyl p-methoxycinnamate, marketed by the company Givaudan under the name Parsol MCX;
(3) liquid derivatives of β,β'-diphenyl acrylate, in particular 2-ethylhexyl α-cyano-α,β'-diphenyl acrylate or octocrylene, marketed by the company BASF under the name UVINUL N539;
(4) derivatives of p-aminobenzoic acid;
(5) 4-methylbenzylidenecamphor marketed by the company Merck under the name EUSOLEX 6300;
(6) 2-phenylbenzimidazole 5-sulphonic acid marketed under the name EUSOLEX 232 by the company Merck;
(7) derivatives of 1,3,5-triazine, in particular: -2,4,6-tris[p-(2'-ethylhexyl-1'-oxycarbonyl)anilino]- 1,3,5-triazine marketed by the company BASF under the name UVINUL T150, and -dioctyl butamidotriazone marketed by the company Sigma 3V under the name UVASORB HEB;
(8) mixtures of these screening agents.

As UVA-screening agents, included are for example:
(1) derivatives of dibenzoylmethane, in particular 4-(tert-butyl)-4'-methoxydibenzoylmethane marketed by the company Givaudan under the name PARSOL 1789;
(2) screening agents which are active in UV-A, such as 1,4-benzene[di(3-methylidene-10-camphorsulphonic)] acid optionally in partially or completely neutralized form, marketed under the name MEXORYL SX by the company Chimex;
(3) derivatives of benzophenone;
(4) silane derivatives or polyorganosiloxanes containing a benzophenone group;
(5) anthranilates, in particular menthyl anthranilate marketed by the company Haarman & Refiner under the name NEO HELIOPAN MA;
(6) compounds comprising per molecule at least two benzoazolyl groups or at least one benzodiazolyl groups;
(7) silicon-containing derivatives of N-substituted benzimidazolylbenzazoles or benzofuranylbenzazoles, in particular those described in Patent Application EP-A-1 028 120;
(8) triazine derivatives, and in particular 2,4-bis{[4(2-ethylhexyloxy)-2-hydroxy]phenyl} -6-(4-methoxyphenyl)- 1,3,5-triazine marketed by the company Ciba Geigy under the name TINOSORB S, and 2,2'-methylenebis[6-(2H-benzotriazol-2-yl)-4-(1,1,3,3-tetramethylbutyl)phenol] marketed by the company Ciba Geigy under the name TINOSORB M;
(9) mixtures thereof.

The pH of the composition according to the invention is not limited and may range, for example, from 5 to 9, preferably from 5.5 to 7.5 and better still from 6 to 7. The pH may, if necessary, be adjusted by adding acids such as hydrochloric acid, citric acid, glycolic acid and any appropriate acid.

According to a preferred embodiment of the invention, the composition is provided in the form of an emulsion, and more particularly in the form of an oil-in-water emulsion.

When the composition is an emulsion, it comprises an oily phase. The proportion of the oily phase of the emulsion is not limited and may range, for example, from 5 to 80% by weight, and preferably from 5 to 50% by weight, relative to the total weight of the composition. The oils, the emulsifiers and optionally the coemulsifiers used in the composition in the form of an emulsion may be chosen from those conventionally used in the cosmetic or dermatological field. The emulsifier and optionally the coemulsifier, while not limited, are generally present in the composition in a proportion ranging from 0.1 to 30% by weight, and preferably from 0.5 to 20% by weight, relative to the total weight of the composition. The emulsion may, in addition, contain lipid vesicles.

Oils which can be used in an emulsion according to the invention include mineral oils (liquid paraffin), oils of plant origin (liquid fraction of shea butter, sunflower oil), oils of animal origin (perhydrosqualene), synthetic oils (hydrogenated polyisobutene, fatty esters such as 2-ethylhexyl palmitate, isopropyl myristate, isononyl isononanoate, cetearyl octanoate), nonvolatile or volatile silicone oils (cyclomethicones such as cyclopentasiloxane) and fluorinated oils (perfluoropolyethers).

The oily phase may also comprise one or more fatty substances other than oils. As fatty substances, there may be mentioned, for example, fatty alcohols such as stearyl alcohol or cetyl alcohol; fatty acids; waxes such as microcrystalline waxes, jojoba wax, lanolin wax or beeswax; gums such as silicone gums (dimethiconol); resins and in particular silicone resins such as trifluoromethyl Cl–4 alkyldimethicone.

The emulsions may generally contain at least one emulsifier chosen from amphoteric, anionic, cationic or nonionic emulsifiers, used alone or as a mixture. The emulsifiers are appropriately chosen depending on the emulsion to be obtained (W/O or O/W).

For the W/O emulsions, there may be mentioned, for example, as emulsifiers, dimethicone copolyols such as the mixture of cyclomethicone and dimethicone copolyol, sold under the name "DC 5225 C" by the company Dow Corning and alkyldimethicone copolyols such as laurylmethicone copolyol sold under the name "Dow Corning 5200 Formulation Aid" by the company Dow Corning and cetyldimethicone copolyol sold under the name Abil EM 90® by the company Goldschmidt.

For the O/W emulsions, emulsifiers include nonionic emulsifiers such as oxyalkylenated (more particularly polyoxyethylenated) esters of fatty acids and glycerol, oxyalkylenated (and more particularly oxyethylenated) esters of fatty acids and sorbitan, oxyalkylenated (oxyethylenated and/or oxypropylenated) esters of fatty acids, oxyalkylenated (oxyethylenated and/or oxypropylenated) ethers of fatty alcohols, sugar esters such as sucrose stearate, and mixtures thereof, and anionic emulsifiers such as, for example, alkyl ether sulphates such as sodium lauryl ether sulphate, sulphosuccinates, isethionates and mixtures thereof, as well as mixtures of the nonionic and anionic emulsifiers mentioned above.

According to a preferred embodiment of the invention, the composition is provided in the form of an O/W emulsion comprising, as emulsifier, one or more polyoxyethylenated and/or polyoxypropylenated ethers of fatty alcohols such as lauryl alcohol or mixtures of C12–C15 fatty alcohols. There may be mentioned in particular, as surfactant of this type, the product marketed under the name Cosmacol PSE by the company Condea Augusta comprising the following mixture (names in CTFA): dimyristyl tartrate/cetearyl alcohol/C12–15 Pareth-7/ PPG-25-Laureth-25.

According to another preferred embodiment of the invention, the composition is provided in the form of an O/W emulsion comprising, as emulsifier, one or more anionic emulsifiers chosen from alkyl ether sulphates, sulphosuccinates, isethionates and mixtures thereof.

Accordingly, one subject of the invention is also an oil-in-water emulsion comprising an oily phase dispersed in an aqueous phase, characterized in that it comprises at least one mixed silicate, at least one polysaccharide and at least one crosslinked poly(2-acrylamido-2-methylpropanesulphonic acid) polymer which is at least 90% neutralized, and at least one emulsifier chosen from polyoxyethylenated and/or polyoxypropylenated fatty alcohol ethers, alkyl ether sulphates, sulphosuccinates, isethionates and mixtures thereof. Preferably, as polyoxyethylenated and/or polyoxypropylenated fatty alcohol ether, the mixture indicated above is used.

Applied to the skin, the composition according to the invention gives a good tightening effect. Thus, it may be used on the skin as a care and/or make-up composition, in particular for tightening the skin, for smoothing it and for attenuating or even immediately removing, and/or reducing the appearance of, fine lines and wrinkles on the skin. By "immediately" it has to be understood an effect that occurs from 15 to 30 minutes after application of the composition.

Accordingly, one subject of the invention is also the cosmetic use of the composition as defined above, for tightening the skin and smoothing it in order to immediately attenuate wrinkles and/or fine lines.

Another subject of the invention is a method for the cosmetic treatment of wrinkles and/or fine lines on the skin, comprising applying to the skin a composition as defined above, in a sufficient quantity to blur the wrinkle by a tightening effect. The sufficient quantity should be such that the quantity of mixed silicate is that indicated above. The invention composition may be prepared by mixing together the noted ingredients, where "mixing together" includes all orders of addition, etc.

The invention is illustrated in more detail in the following examples, but is not limited thereby. The quantities are in percentage by weight, unless otherwise stated. Example 1: O/W emulsion

| Phase A: | |
|---|---|
| Dimyristyl tartrate/cetearyl alcohol/C12–15 Pareth-7/PPG-25-Laureth-25 (Cosmacol PSE) | 1.5% |
| Silicone oil | 5% |
| Vegetable oil | 5% |
| Preservative | 0.15% |
| Ethylhexyl methoxycinnamate (screening agent) | 1% |
| Phase B: | |
| Glycerin | 5% |
| Preservative | 0.5% |
| Disodium EDTA (sequestrant) | 5% |
| Hostacerin AMPS | 0.4% |

-continued

| | |
|---|---|
| Phase C: | |
| Xanthan gum | 0.2% |
| Phase D: | |
| Laponite XLG | 3% |
| Demineralized water | qs 100 |

Procedure: Phases A and B are heated separately to approximately 75° C., with stirring, and then phase A is poured into phase B, with stirring. Phase C is then added and the heating is stopped while the stirring is maintained. Phase D is prepared by sprinkling Laponite in water, with stirring, at room temperature: a fairly thick colorless transparent gel is obtained in 15–20 min and it is added to the emulsion previously obtained and cooled to a temperature of 40–50° C. The stirring is maintained until the temperature returns to room temperature (about 20 to 25° C.).

A cream is obtained which has an immediate tightening effect, making it possible to blur fine lines on the face. This tightening effect is demonstrated by the method for measuring retraction using an extensometer, described below:

The principle consists in measuring, before treatment and after treatment, the length of a test piece of isolated *stratum corneum* and determining the percentage retraction of the test piece.

Test pieces of 1 cm×0.4 cm of *stratum corneum* are used which have a thickness ranging from 10 to 20 μm and which are placed on the MTT 610 extensometer marketed by the company DIASTRON. The test piece is placed between two jaws and then left for 12 hours in an atmosphere at 30° C. and 40% relative humidity. The test piece is subjected to traction at the rate of 2 mm/minute by a length of between 5 and 10% of the original length in order to determine the length $L_1$ from which the test piece begins to exert a force on the jaws and which is detected by the apparatus. The test piece is then relaxed and then 2 mg of the emulsion of Example 1 are applied to the *stratum corneum*. After complete evaporation of the composition, the test piece is subjected to traction under the same conditions as those described above in order to also determine the length $L_2$ for the treated test piece. The percentage retraction is determined by the 5 relationship: $100 \times (L_2-L_1)/L_1$.

For the emulsion of Example 1, the percentage retraction of the *stratum corneum* test piece is −1.6+/−0.4.

The tightening effect is also demonstrated on models: a photo is taken before the application of any product and then after having applied the emulsion according to the invention and the photographs are compared. A marked decrease in the visibility of the wrinkles (particularly the crow's-foot and under the eyes) is observed.

French patent application 0014175 filed Nov. 6, 2000 is incorporated herein by reference, as are all documents referred to in this application. Where a range is stated herein it includes all values therebetween and all subranges therebetween as if specifically written out. Those of ordinary skill know how to apply and use the invention compositions based on the above description, for example by applying to, e.g., the skin 0.5–5 g (or more or less as desired) of invention composition once or more often each day. Skin to be particularly targeted is facial skin showing wrinkles and/or fine lines, and areas of the face expected to show wrinkles and/or fine lines, such as with age.

What is claimed is:

1. A composition comprising at least one mixed silicate, at least one polysaccharide, and at least one crosslinked poly(2-acrylamido-2-methyl-propanesulphonic acid) polymer which is at least 90% neutralized.

2. The composition according to claim 1, wherein the mixed silicate is selected from the group consisting of montmorillonites, hectorites, bentonites, beidellite and saponites.

3. The composition according to claim 1, wherein the mixed silicate is in the form of a powder whose particles have a mean size ranging from 5 to 1000 nm.

4. The composition according to claim 1, wherein the mixed silicate is a phyllosilicate.

5. The composition according to claim 1, wherein the mixed silicate belongs to the hectorite family.

6. The composition according to claim 1, wherein the mixed silicate is a laponite.

7. The composition according to claim 1, wherein the mixed silicate is present in a quantity ranging from 0.01 to 10% by weight relative to the total weight of the composition.

8. The composition according to claim 1, wherein the mixed silicate is present in a quantity ranging from 0.05 to 5% by weight relative to the total weight of the composition.

9. The composition according to claim 1, wherein the polysaccharide is selected from the group consisting of cellulose derivatives; galactomannans and their derivatives; algal extracts; plant exudates; microbial exudates, and mixtures thereof.

10. The composition according to claim 1, wherein the polysaccharide is xanthan gum.

11. The composition according to claim 1, wherein the polysaccharide is present in a quantity ranging from 0.01 to 8% by weight relative to the total weight of the composition.

12. The composition according to claim 1, wherein the polysaccharide is present in a quantity ranging from 0.05 to 5% by weight relative to the total weight of the composition.

13. The composition according claim 1, wherein the poly(2-acrylamido-2-methylpropanesulphonic acid) polymer comprises, randomly distributed:

a) from 90 to 99.9 by weight of units having the following general formula (I):

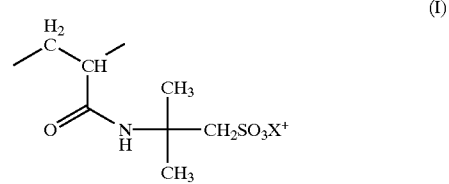

in which $X^+$ denotes a cation or a mixture of cations, it being possible for at most 10 mol % of the cations $X^+$ to be protons $H^+$;

b) from 0.01 to 10% by weight of crosslinking units obtained from at least one monomer having at least two olefin double bonds, the proportions by weight of a) and b) being defined relative to the total weight of the polymer.

14. The composition according to claim 13, wherein the poly(2-acrylamido-2-methylpropanesulphonic acid) polymer comprises from 98 to 99.5 by weight of units of formula (I) and from 0.2 to 2% by weight of crosslinking units.

15. The composition according to claim 13, wherein in formula (I), the cation $X^+$ is $NH_4^+$.

16. The composition according to claim 14, wherein in formula (I), the cation $X^+$ is $NH_4^+$.

17. The composition according to claim 13, wherein the crosslinking units in the polymer arise from monomers of the following general formula (II)

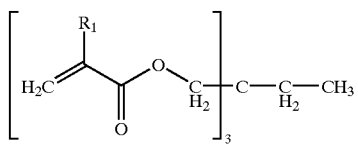

(II)

in which $R_1$ denotes hydrogen or a $C_1$–$C_4$ alkyl.

18. The composition according to claim 17, wherein the poly(2-acrylamido-2-methylpropanesulphonic acid) polymer is crosslinked with trimethylolpropane triacrylate.

19. The composition according to claim 1, wherein the quantity of crosslinked poly(2-acrylamido-2-methylpropanesulphonic acid) polymer ranges from 0.1 to 10% by weight relative to the total weight of the composition.

20. The composition according to claim 1, further comprising a physiologically acceptable aqueous medium.

21. The composition according to claim 1, further comprising one or more active ingredients selected from the group consisting of vitamins, keratolytic or prodesquamating agents, anti-free radical agents, sunscreens, moisturizing agents, ceramides, retinoids, tightening polymers, DHEA and its derivatives, and coenzyme Q10.

22. The composition according to claim 1, wherein said composition has a pH ranging from 5 to 9.

23. The composition according to claim 1, wherein said composition is in the form of an emulsion.

24. The composition according to claim 23, wherein said composition is in the form of an O/W emulsion.

25. The composition according to claim 24, further comprising at least one emulsifier selected from the group consisting of nonionic emulsifiers, anionic emulsifiers and mixtures thereof.

26. An oil-in-water emulsion comprising an oily phase dispersed in an aqueous phase, wherein said emulsion further comprises at least one mixed silicate, at least one polysaccharide, at least one crosslinked poly(2-acrylamido-2-methylpropanesulphonic acid) polymer which is at least 90% neutralized, and at least one emulsifier selected from the group consisting of polyoxyethylenated and/or polyoxypropylenated fatty alcohol ethers, alkyl ether sulphates, sulphosuccinates, isethionates and mixtures thereof.

27. The emulsion according to claim 26, wherein the emulsifier is a mixture of dimyristyl tartrate/cetearyl alcohol/C12–15 Pareth-7/ PPG-25-Laureth-25.

28. A method for tightening the skin and smoothing it so as to immediately attenuate wrinkles and/or fine lines, comprising applying the composition of claim 1 to the skin.

\* \* \* \* \*

UNITED STATES PATENT AND TRADEMARK OFFICE
CERTIFICATE OF CORRECTION

PATENT NO. : 6,630,131 B2  
DATED : October 7, 2003  
INVENTOR(S) : Veronique Chevalier et al.

It is certified that error appears in the above-identified patent and that said Letters Patent is hereby corrected as shown below:

Column 10,
Line 34, "according claim" should read -- according to claim --.

Signed and Sealed this

Twenty-third Day of December, 2003

JAMES E. ROGAN
*Director of the United States Patent and Trademark Office*